United States Patent [19]
Daniel

[11] Patent Number: 5,529,571
[45] Date of Patent: Jun. 25, 1996

[54] SURGICAL RETRACTOR/COMPRESSOR

[76] Inventor: Elie C. Daniel, 402 First Ave., Mendota, Ill. 61342

[21] Appl. No.: 373,008

[22] Filed: Jan. 17, 1995

[51] Int. Cl.⁶ .......................... A61B 17/02; A61B 17/28
[52] U.S. Cl. .................. 600/219; 600/202; 600/210; 600/213; 600/218; 600/245; 403/90; 606/207
[58] Field of Search ................................. 600/201, 202, 600/206, 210, 213, 215, 216, 218, 219, 222, 223, 245; 606/105, 191, 205, 207, 208; 604/106; 403/90

[56] References Cited

U.S. PATENT DOCUMENTS

| | | | |
|---|---|---|---|
| 1,317,903 | 10/1919 | Whimster | 403/90 |
| 4,457,300 | 7/1984 | Budde | 128/20 |
| 4,562,832 | 1/1986 | Wilder et al. | 128/20 |
| 4,945,896 | 8/1990 | Gade | 600/202 |
| 5,020,933 | 6/1991 | Salvestro et al. | 403/90 |
| 5,297,538 | 3/1994 | Daniel | 600/215 |
| 5,346,489 | 9/1994 | Levy et al. | 606/15 |

Primary Examiner—Richard J. Apley
Assistant Examiner—Kelly McGlashen
Attorney, Agent, or Firm—Rockey, Rifkin and Ryther

[57] ABSTRACT

The surgical instrument of the invention consists of a pair of arms hinged together at an intermediate point for relative pivoting movement. The arms are provided with obliquely oriented handles at one end thereof. The opposite ends of the arms support removable posts having means for removably securing a plurality of different retractor or compressor heads thereto. The posts are pivotably connected to the arms to allow the posts to achieve a variety of orientations relative to the arms. A variety of retractor and compressor heads and different shaped posts are provided to allow the instrument to be used in a wide variety of surgical procedures. Separate serrated locking mechanisms are provided to lock the arms in either a retraction or compression position. In one embodiment the posts are secured to one another such that they undergo parallel retraction/compression.

30 Claims, 2 Drawing Sheets

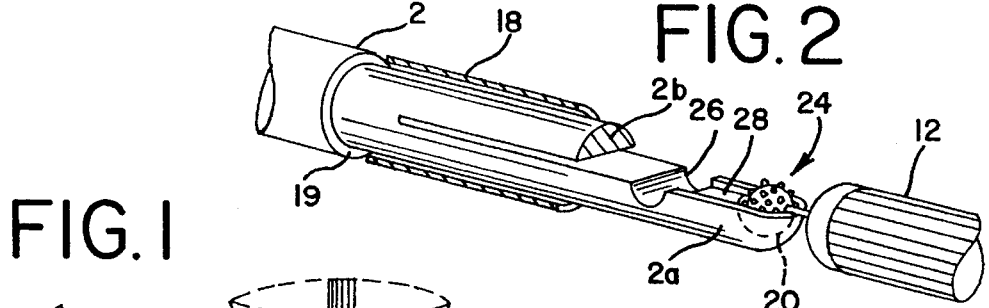
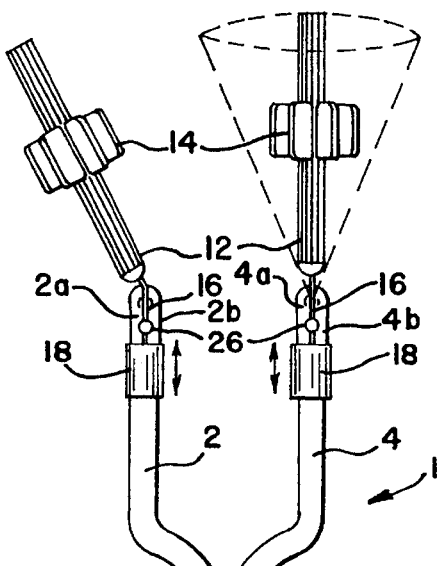
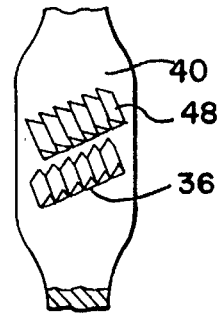
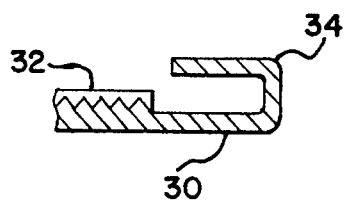
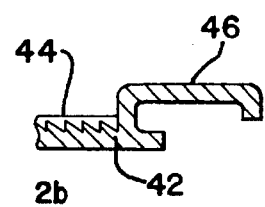

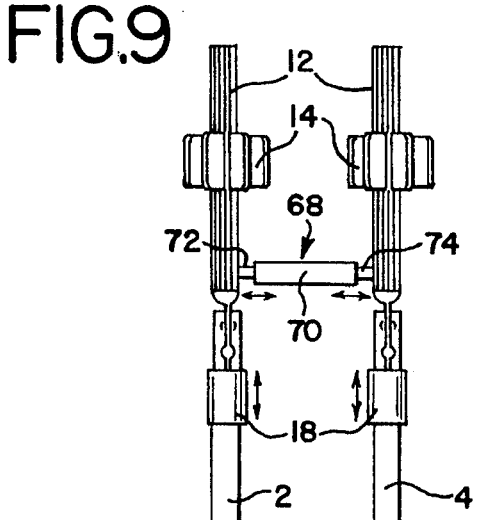
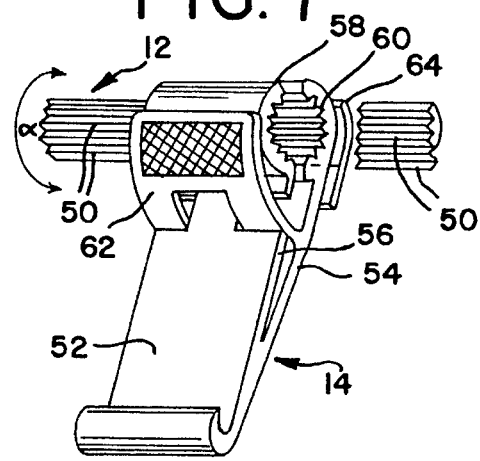
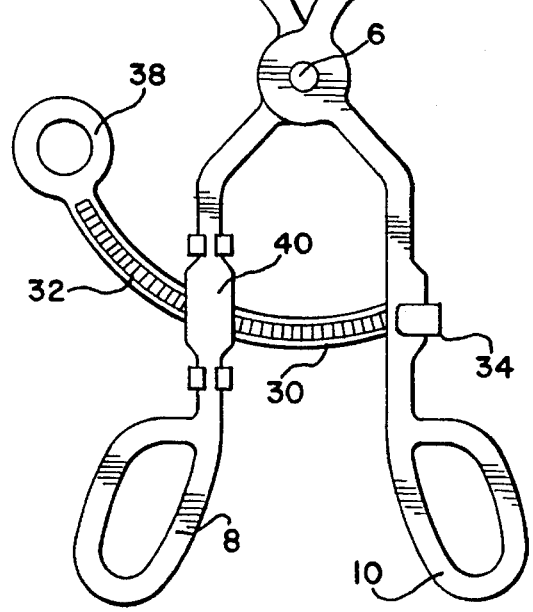
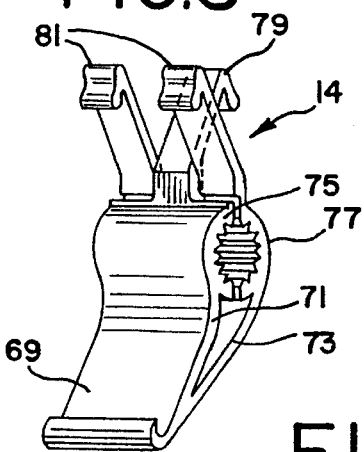
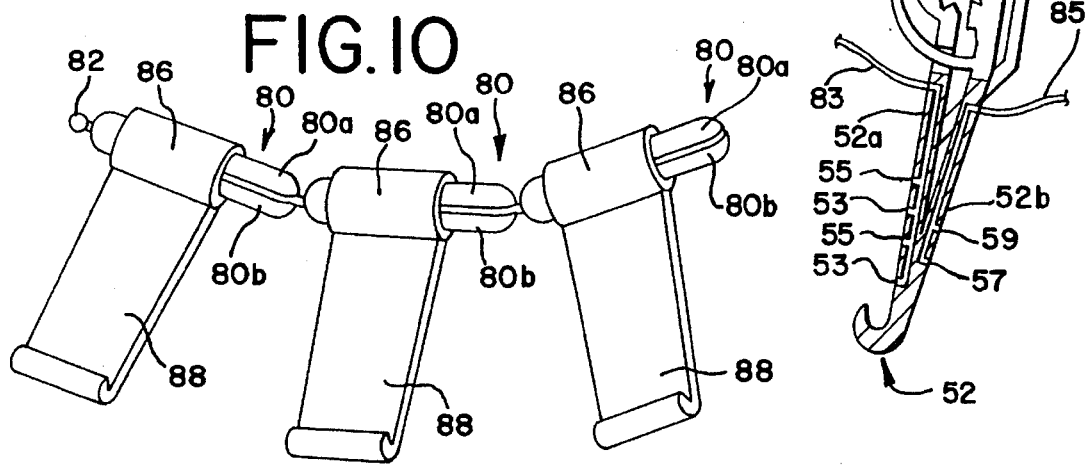

5,529,571

SURGICAL RETRACTOR/COMPRESSOR

BACKGROUND OF THE INVENTION

The invention relates, generally, to medical instruments and, more particularly, to a combined surgical retractor/compressor.

Retractors are used during surgery to retract tissue, spread ribs and perform similar functions. Compressors are used to compress and hold tissue, bone and the like. Both retractors and compressors typically include a pair of elongated arms pivotally connected intermediate their ends for relative motion. The arms are typically symmetrical and include either a retractor or compressor head fixed to the ends thereof designed to perform a specific surgical procedure.

While such devices are widely used, the symmetry of the arms limits their use and the fact that the heads are fixed to the arms necessitates the use of separate instruments for different surgical procedures. Moreover, retractors cannot be used for compression and compressors cannot be used for retraction. Thus, an improved surgical tool that can be used in a variety of surgical applications is desired.

SUMMARY OF THE INVENTION

The surgical instrument of the invention overcomes the above-noted shortcomings and consists of a pair of arms hinged together at an intermediate point for relative pivoting movement. The arms are provided with obliquely oriented handles at one end thereof. The opposite ends of the arms support removable posts having means for removably securing a plurality of different retractor or compressor heads thereto. The posts are pivotably connected to the arms to allow the posts to achieve a variety of orientations relative to the arms. A variety of retractor and compressor heads and different shaped posts are provided to allow the instrument to be used in a wide variety of surgical procedures. The heads can include fiber optics to allow viewing of the surgical situs or to determine blood oxygen levels. Separate serrated locking mechanisms are provided to lock the arms in either a retraction or compression position. In one embodiment the posts are secured to one another such that they undergo parallel retraction/compression.

BRIEF DESCRIPTION OF THE DRAWINGS

FIG. 1 is a side view of the retractor of the invention.

FIGS. 2 and 3 are partial section views of two alternate embodiments of the arms of the retractor shown in FIG. 1.

FIG. 4 is a detailed view of one of the arms of the invention.

FIGS. 5 and 6 are partial section views of the locking mechanisms of the invention.

FIGS. 7 and 8 are alternate embodiments of the retractor/compressor heads of the invention.

FIG. 9 shows an alternate embodiment of the invention where the posts are mounted for parallel retraction/compression.

FIG. 10 shows an alternate embodiment of the arms of the invention.

FIG. 11 shows a partial cross-section view of one of the retractor compressor heads having fiber optics capabilities.

DETAILED DESCRIPTION OF THE DRAWINGS

Referring more particularly to the figures, the surgical instrument of the invention is shown generally at 1 consisting of a pair of arms 2 and 4 pivotally connected at hinge 6 such that the arms can pivot relative to one another. Arms 2 and 4 are provided with obliquely angled handles 8 and 10, respectively, to facilitate their manipulation. The arms are arranged such that when handles 8 and 10 are moved towards one another the upper portion of arms 2 and 4 are moved away from one another and vice versa. Moreover, arms 2 and 4 can be curved to allow manipulation of the arms around obstructing body parts if desired. The arms 2 and 4 support posts 12 which, in turn, support retractor/compressor heads 14 as will hereinafter be described.

Referring more particularly to FIGS. 1 and 2, the ends of arms 2 and 4 are identical and include slots 16 extending from the distal ends thereof. The slots 16 are centrally positioned in the arms and divide the arms 2 and 4 into sections 2a, 2b and 4a, 4b, respectively. As another embodiment best shown in FIG. 2, the ends of arms 2 and 4 are tapered such that the arms gradually become thicker towards the ends thereof. The sections can flex slightly relative to one another such that the space between the sections created by slot 16 can be increased or decreased. A collet 18 is mounted on each of arms 2 and 4 and can be slid over the sections 2a, 2b and 4a, 4b to flex the sections toward one another thereby to lessen the space between the sections. Shoulders 19 are formed on arms 2 and 4 to prevent the collets 18 from sliding down the length of the arms.

An alternate embodiment of the arms is shown in FIG. 3. Specifically, arm 2 is shown formed with spiral projections, splines or screw threads 21 that mate with grooves, splines or screw threads 23 formed on collet 18. Thus, to move the collet over portions 2a and 2b, it must be turned or screwed as it is slid toward the ends of the arm. It is to be understood that an identical arrangement can be used on arm 4. This arrangement provides a more secure engagement between the collet and arms and minimizes the likelihood that the collet will slip. It is also contemplated that the projections or splines on the collet and arms could extend linearly parallel to the longitudinal axis of the arms if desired. Or, the projections or splines on the arms and collets could extend circumferentially, perpendicular to the longitudinal axis of the arms such that the splines are simply forced over one another.

Referring again to FIG. 2, located at the ends of each of arms 2 and 4 are sockets for receiving the ball 24 from one of the posts 12. Because arms 2 and 4 are identical in this regard, specific reference will be made only to arm 2. A through hole 26 extends through arm 2 and may be centered relative to slot 16 if desired. Through hole 26 is connected to socket 20 by grooved channel 28. If desired, hole 26 need only extend partially through the arm.

The ball 24 can be provided with a pebbled or ridged surface to increase the mechanical and frictional engagement between the ball and socket 20 as best shown in FIG. 2. Likewise, socket 20 can be provided with a similar surface to further increase the engagement. The ball can also have other than a circular cross-section if desired.

To connect a posts 12 to arms 2 and 4, one mechanism for engagement of the ball 24 to the socket 20 can be established by having the ball 24 of the post 12 inserted into through hole 26. Another would be to push the ball into socket 20 through channel 28. As the ball is forced toward socket 20, portions 2a and 2b are forced apart allowing the ball to pass through passage 28 and enter socket 20.

Once the ball 24 is located in socket 20, the post 14 can be positioned at any angle relative to the arm within the conical volume bounded by the dashed line zone in FIG. 1. Once the post is positioned as desired, the collet 18 is slid over the end of the arms forcing the arm portions 2a and 2b toward one another thereby to lock the ball 24 relative to socket 20 and the post in the desired position. The posts can be repositioned to provide a wide variety of compression and retraction angles as dictated by the specific surgical procedure. Moreover, the posts can include female sockets at the ends thereof, such as those at the ends of arms 2 and 4, such that the posts can be connected together in series.

Referring more particularly to FIGS. 1, 4, 5 and 6, locking mechanisms 30 and 42 are provided for fixing the position of arms 2 and 4 relative to one another in a retraction mode or compression mode, respectively. One embodiment of a locking mechanism 30 includes projections 32 and is removably fixed to arm 4 by clip 34. Projections 32 are engageable with a corresponding set of projections 36 formed on enlarged portion 40 of arm 2 to lock the arms in a retracting position. A loop 38 is provided at the end of member 30 to allow the instrument to be secured to a surgical drape. Locking mechanisms 30 and 42 are curved to follow the path of travel of arms 2 and 4 as they are pivoted relative to one another.

Referring to FIG. 6, a second locking mechanism 42 is provided that is identical to mechanism 30 except that serrations 44 face the opposite direction and clip 46 is configured to resist a compressive force. Locking mechanism 42 is engageable with a second set of projections 48 formed on enlarged portion 40 to lock the arms in a compressing position. Locking mechanisms 30 and 42 allow the instrument of the invention to be used as a retractor and a compressor, respectively. It is to be understood that locking mechanisms 30 and 42 can be fixed to arm 4 by any suitable mechanism.

Referring more particularly to FIGS. 7 and 8, the retractor or compressor heads 14 and posts 12 are shown in greater detail. The posts 12 consist of a plurality of longitudinally extending projections, serrations or splines 50 extending for substantially the length thereof and arranged about substantially the periphery of the post. The head 14 shown in FIG. 7 consists of a tissue contacting portion 52 having a pair of flexible flanges 54 and 56 extending therefrom. The flanges 54 and 56 terminate in portions 58 and 60, respectively, which include projections, serrations or splines dimensioned to mate with the projections, serrations or splines formed on the posts 12. Extending from flanges 54 and 56 are tabs 62 and 64 respectively, arranged such that when the tabs are squeezed together the portions 58 and 60 will be separated a distance sufficient to disengage from the post 12. A stop is provided to prevent overpressure on the flanges thereby to maintain their resiliency. Other mechanisms can be used to disengage the portions 58 and 60 from the post if desired. The use of the projections or serrations allows the head 14 to be positioned anywhere along the length of post 12 and at any radial angle $\alpha$. Alternatively, the posts and flanges can be provided without the projections, serrations or splines such that the surface of posts 12 and portions 58 and 60 are relatively smooth. In this arrangement the head will be maintained in position on the post by friction. These surfaces can be pebbled or roughened to increase the friction forces.

An alternate embodiment of head 14 is shown in FIG. 8 and consists of a tissue contacting portion 69 having flanges 71 and 73 extending therefrom. Flanges 71 and 73 include portions 75 and 77, respectively, having projections or serrations that engage projections or serrations 50 formed in the posts 12. Extending from portions 75 and 77 are finger tabs 79 and 81 that are arranged such that when the tabs are squeezed together, portions 75 and 77 will be disengaged from the posts 12. Like the embodiment of FIG. 7, the head shown in FIG. 8 can be positioned anywhere along the length of the post and at any angle $\alpha$.

The specific configuration of the posts can be modified, if desired. For example, the post can be provided with a curved profile or with a generally S-shape. The specific shape chosen for the post will be dictated by the application in which the instrument is used. While a number of alternate shapes for the posts have been described, it is to be understood that the post shape is not limited to those discussed above and can take any desired shape. Moreover, the lengths of the posts can be varied as desired.

Referring more particularly to FIG. 11, it is further contemplated that heads 14 include fiber optics to allow the surgeon to receive information about the operation situs. Specifically, each head 14 includes a tissue contacting portion 52 having a tissue contacting face 52a that actually contacts the tissue and a noncontacting face 52b that faces away from the tissue during use.

Located on the tissue contacting face 52a are a plurality of fiber optics light emitters 53 and receptors 55 connected to a fiber optics cable 83. The fiber optics cable can run internally or externally of the head 16 and can extend either internally or externally of the posts and arms. The fiber optics cable is connected to an oximeter for measuring the blood oxygen level in the tissue. A suitable oximeter system is sold by Criticare Systems, Inc. of Waukesha, Wis.

The oximeter detects light coming from the light receptor after it has been reflected off of the tissue. The oximeter, by analyzing the light received, can determine the $O_2$ saturation in the tissue, as is well known. Because tissue, when it is subject to pressure such as by retractor head 14, will lose $O_2$ saturation, it is desirable to known when that oxygen level becomes undesirably low such that the retractor head can be moved to a different tissue area to prevent post-operative gangrene or other tissue damage.

Located on the non-tissue contacting face 52b is a light source 57 and a fiber optic camera 59. The light source will serve to illuminate the surgical field while the camera will allow surgical procedures to be observed in areas that would otherwise be inaccessible. The camera and light source are connected via fiber optics cable 85 to a suitable monitor (not shown). A suitable fiber optics camera is commercially available from Smith & Nephew, Dionics Division of Andovar, Mass. In addition to the fiber optics, it is also possible to attach other devices to the heads such as suction, irrigation or the like.

An alternate embodiment of the invention is shown in FIG. 9 and consists of the arms 2 and 4, posts 12 and heads 14 described with reference to FIG. 1. Additionally, a linkage 68 is disposed between and connected to posts 12. Linkage 68 consists of a cylinder 70 having reciprocating pistons 72 and 74 extending from either end thereof. The ends of the pistons 72 and 74 are rigidly connected to the posts 14 such that there is no movement between these elements. As a result of linkage 68, when the handles 8 and 10 are squeezed to spread arms 2 and 4 for retraction, the linkage 68 maintains the posts 12 parallel to one another as they are separated even though the arms 2 and 4 are pivoting relative to one another. In the preferred embodiment, the pistons are releasably connected to the posts by a snap-fit or threaded engagement such that the retractor can be converted from a parallel retractor (FIG. 9) to a pivoting retractor (FIG. 1).

A further embodiment is illustrated in FIG. 10 where a plurality of posts 80 are connected to one another by the ball and socket joint described with reference to FIGS. 1 and 2.

Specifically, each post 80 includes portions 80a and 80b that can flex slightly to retain the ball 82 of the adjacent post therebetween. The collets 86 can be slid over portions 80a and 80b to clamp the balls 82 in the desired position. In the illustrated embodiment, each collet includes a tissue contacting member 88 formed integrally therewith. The use of multiple posts allows the retractor to be formed to a virtually infinite number of shapes depending on the needs of the surgeon.

As will be apparent from the foregoing description, the retractor of the invention can be configured as desired by the surgeon to perform virtually any retraction or compression procedure. Although the invention has been described in some detail with respect to the drawings, it will be understood that the foregoing description was offered merely by way of example and that numerous changes can be made to the construction and details of the device without departing from the spirit and scope of the invention.

What is claimed is:

1. A surgical instrument comprising:
   a) first and second arms pivotally secured together at an intermediate point to allow relative pivoting movement;
   b) a plurality of posts, each post including a first set of projections extending for substantially the length thereof and provided about substantially the entire periphery of the post;
   c) means for removably securing said posts to said arms whereby different posts can be secured to said arms depending on the surgical procedure to be performed, said means for removably securing allowing the posts to be positioned at varying angles relative to the arms;
   d) a plurality of surgical heads including a first set of means for contacting tissue; and
   e) means for removably securing the surgical heads to the posts including a second set of projections formed on each surgical head for releasably engaging said first set of projections such that the surgical head can be movably positioned along the length of the post and can be positioned at varying angles relative thereto whereby different surgical heads can be secured to said arms depending on the surgical procedure being performed.

2. The surgical instrument according to claim 1, wherein the means for removably securing the posts to the arms includes a ball and socket connector.

3. The surgical instrument according to claim 2, wherein the means for removably securing the posts to the arms also includes means for locking the posts at the desired angle.

4. The surgical instrument according to claim 1, further including means for locking said arms in compression or retraction comprising third and fourth sets of projections formed on said second arms, a first locking mechanism releasably secured to the first arm and engageable with the third set of projections on the fourth arm to lock the arms in a retracting position and a second locking mechanism releasably secured to the first arm and engageable with the fourth set of projections on the second arm to lock the arms in a compressing position.

5. The surgical instrument according to claim 1, wherein the posts support another post, said another post being movably positioned at any angle and including means for supporting surgical heads.

6. The surgical instrument according to claim 1, wherein the surgical heads include means for sensing the blood oxygen level of the tissue.

7. The surgical instrument according to claim 1, wherein the surgical heads include means for viewing the surgical area.

8. The surgical instrument according to claim 6, wherein the means for sensing includes fiber optics emitter and detector on said heads and an oximeter.

9. The surgical instrument according to claim 7, wherein the means for viewing includes a fiber optics camera.

10. The surgical instrument according to claim 2, wherein the ball and socket includes means for enhancing the engagement therebetween.

11. The surgical instrument according to claim 10, wherein said means for enhancing engagement includes projections formed on the ball.

12. The surgical instrument according to claim 3, wherein the means for locking includes slotted ends of the arms forming arm sections which are movable towards one another to clamp the ball therebetween.

13. The surgical instrument according to claim 12, including a collet for moving said portions toward one another.

14. The surgical instrument according to claim 13, wherein said collet and said arms include means engageable with one another.

15. A surgical instrument comprising:
   a) first and second arms pivotally secured together at an intermediate point to allow relative pivoting movement;
   b) a plurality of posts;
   c) means for removably securing said posts to said arms whereby different posts can be secured to said arms depending on the surgical procedure to be performed, said means for removably securing allowing the posts to move relative to the arms, the limit of the movement of the posts defining a conical volume;
   d) a plurality of surgical heads including means for contacting tissue; and
   e) means for removably securing the surgical heads to the posts such that the surgical head can be movably positioned along the length of the post and can be positioned at varying angles relative thereto whereby different surgical heads can be secured to said arms depending on the surgical procedure being performed.

16. The surgical instrument according to claim 15, wherein the means for removably securing the posts to the arms includes a ball and socket connector.

17. The surgical instrument according to claim 16, wherein the means for removably securing the heads to the posts includes projections on the post mating with projections on the heads.

18. The surgical instrument according to claim 15, further including means for locking said arms in compression or retraction comprising first and second sets of projections formed on said second arms, a first locking mechanism releasably secured to the first arm and engageable with the first set of projections on the second arm to lock the arms in a retracting position and a second locking mechanism releasably secured to the first arm and engageable with the second set of projections on the second arm to lock the arms in a compressing position.

19. The surgical instrument according to claim 15, wherein the posts support another post, said another post being movably positioned relative to the post and including means for supporting surgical heads.

20. The surgical instrument according to claim 15, wherein said means for securing said posts to said arms includes means for locking said posts to the arms at different angles such that the angle of the posts relative to the arms can be varied.

21. The surgical instrument according to claim 20, wherein said means for locking fixes the posts at any angle relative to the arms.

22. The surgical instrument according to claim 15, wherein the surgical heads include means for sensing the blood oxygen level of the tissue.

23. The surgical instrument according to claim 15, wherein the surgical heads include means for viewing the surgical area.

24. The surgical instrument according to claim 22, wherein the means for sensing includes fiber optics emitter and detector on said heads and an oximeter.

25. The surgical instrument according to claim 23, wherein the means for viewing includes a fiber optics camera.

26. The surgical instrument according to claim 16, wherein the ball and socket include means for enhancing the engagement therebetween.

27. The surgical instrument according to claim 26, wherein said means for enhancing engagement includes projections formed on the ball.

28. The surgical instrument according to claim 20, wherein the means for locking includes slotted ends of the arms forming arm sections which are movable towards one another to clamp the ball therebetween.

29. The surgical instrument according to claim 28, including a collet for moving said portions toward one another.

30. The surgical instrument according to claim 29, wherein said collet and said arms include means engageable with one another.

* * * * *

UNITED STATES PATENT AND TRADEMARK OFFICE
CERTIFICATE OF CORRECTION

PATENT NO. : 5,529,571
DATED : June 25, 1996
INVENTOR(S) : Elie C. Daniel

It is certified that error appears in the above-indentified patent and that said Letters Patent is hereby corrected as shown below:

Column 5,

In claim 1, line 14,

"a first set of" should be deleted.

In claim 4, line 6,

"fourth" should be changed to --second--.

Signed and Sealed this

Tenth Day of September, 1996

Attest:

BRUCE LEHMAN

Attesting Officer

Commissioner of Patents and Trademarks